United States Patent [19]

Gordon

[11] 4,375,397
[45] Mar. 1, 1983

[54] PROCESS FOR PREPARING 3-METHYLENE CEPHALOSPORINS

[75] Inventor: Eric M. Gordon, West Trenton, N.J.

[73] Assignee: E. R. Squibb & Sons, Inc., Princeton, N.J.

[21] Appl. No.: 666,989

[22] Filed: Mar. 15, 1976

[51] Int. Cl.³ .............................................. B01J 19/12
[52] U.S. Cl. ................................................. 204/158 R
[58] Field of Search ..................................... 204/158 R

[56] References Cited

U.S. PATENT DOCUMENTS 3,898,142  8/1975  Gold ............................... 204/158 R

FOREIGN PATENT DOCUMENTS 1403002  8/1975  United Kingdom ............ 260/243 C

Primary Examiner—Howard S. Williams
Attorney, Agent, or Firm—Lawrence S. Levinson; Donald J. Barrack

[57] ABSTRACT

Photolysis of azetidin-2-one derivatives having the formula

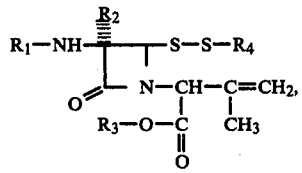

wherein $R_1$ is acyl, $R_2$ is hydrogen or α-methoxy, $R_3$ is hydrogen, alkyl, 2,2,2-trichloroethyl, trimethylsilyl, diphenylmethyl, benzyl, 4-methoxybenzyl, or 4-nitrobenzyl, and $R_4$ is an aromatic heterocyclic group, yields 3-methylene cephalosporins.

4 Claims, No Drawings

PROCESS FOR PREPARING 3-METHYLENE CEPHALOSPORINS

BACKGROUND OF THE INVENTION

There is intense interest in the pharmaceutical field in the development of synthetic routes for the conversion of penicillins to cephalosporin antibiotics.

3-Methylene cephalosporins of the formula

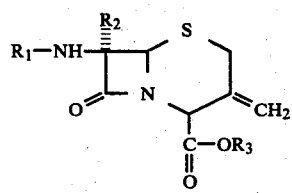

are known to be useful intermediates for the preparation of cephalosporin antibiotics that are effective against gram-negative bacteria such as *Escherichia coli, Broteus vulgaris, Proteus mirabilis, Proteus morganii, Salmonella schonmuelleri, Klebsiella pneumoniae* AD, *Klebsiella pneumoniae* B, and *Paracolobactrum arizoniae* and gram-positive bacteria including *Staphylococcus aureus, Streptococcus pyogenes* and *Diplococcus pneumoniae;* see, for example, U.S. Pat. No. 3,883,518 issued May 13, 1975 to Ponticello et al. In formula I, and throughout the specification, the symbol $R_1$ can be an acyl group, $R_2$ can be hydrogen or α-methoxy, and $R_3$ can be hydrogen, alkyl of 1 to 4 carbon atoms, 2,2,2-trichloroethyl, trimethylsilyl, diphenylmethyl, benzyl, 4-methoxybenzyl, or 4-nitrobenzyl.

The treatment of a 3-methylene cephalosporin of formula I with an organic base promotes isomerization to useful desacetoxy cephalosporins; see, for example, Chauvette et al., J. Org. Chem., 38, 2994 (1973). The oxidative fission of 3-methylene cephalosporins of formula I provides useful 3-hydroxy cephems; see, for example, Netherlands patent 7309136.

SUMMARY OF THE INVENTION

The process of this invention provides for the preparation of 3-methylene cephalosporins from penicillin precursors. More specifically, the process of this invention comprises the conversion of an azetidin-2-one derivative having the formula

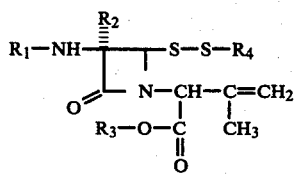

to a 3-methylene cephalosporin having the formula

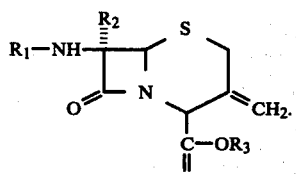

In the above formulas $R_1$, $R_2$ and $R_3$ are as defined above, and $R_4$ can be an aromatic heterocyclic group. The conversion is accomplished by photolysis.

DETAILED DESCRIPTION OF THE INVENTIONS

3-Methylene cephalosporins of formula I can be prepared by photolysis of an azetidin-2-one derivative of formula II. The reaction is preferably run in an inert atmosphere (e.g., argon or nitrogen) and in an organic solvent. The preferred solvents are the halogenated hydrocarbons, e.g., methylene chloride and chloroform. Other solvents may be used, however, and these can be exemplified by hydrocarbons such as benzene and toluene, alcohols such as methanol or t-butanol, acetonitrile, acetone, ethyl acetate, acetic acid, tetrahydrofuran, ethyl ether, dimethylformamide, nitromethane and others.

The light source used must of course emit light of a wavelength that is absorbed by the azetidin-2-one reactants of formula II. The azetidin-2-ones of formula II absorb light having a wavelength of from about 230 nanometers to 500 nanometers. The most common type of light source used is a mercury lamp. It has been found that a commercially available medium pressure mercury arc lamp with a Pyrex filter is a convenient light source for the photolytic reaction of this invention.

The time and temperature of the reaction are not critical. The reaction can be conveniently run at room temperature for a period that will vary according to the intensity of the light source used.

The concentration of the azetidin-2-one in the organic solvent is not a critical factor in the process of this invention. However, use of a dilute solution of reactant will minimize the possibility of side reactions such as dimerization. A concentration range of $3 \times 10^{-3}$ mole/liter to $3 \times 10^{-2}$ mole/liter has been found to be optimal.

The azetidin-2-one derivatives of formula II are readily prepared (using the process described in British Pat. Nos. 1,403,002 and 1,403,003) from the corresponding penicillanic acid derivatives having the formula

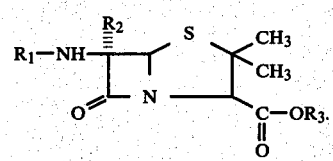

Oxidation of a penicillanic acid derivative of formula III with an oxidizing agent either alone or in the presence of a catalytic amount of a compound of a metal of Group Vb or VIb of the Periodic Table yields the corresponding penicillanic acid derivative having the formula

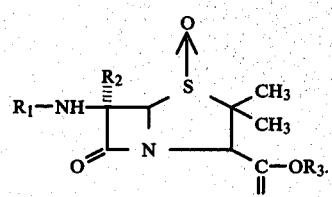

Among the oxidizing agents which can be used are hydrogen peroxide and the peracids such as perbenzoic acid, m-chloroperbenzoic acid, percarbonic acid or periodic acid. Among the catalysts which can be used are tungstic acid, molybdic acid and vanadic acid, or an alkali metal or alkaline earth metal thereof.

An oxidized penicillanic acid derivative of formula IV can be reacted with a mercaptan having the formula $$R_4\text{-SH} \qquad\qquad V$$

to yield the corresponding azetidin-2-one derivative of formula II. The reaction can be run in an organic solvent, preferably under reflux conditions.

The aromatic heterocyclic group $R_4$ preferably contains 1,2, or 3 nitrogen, oxygen, and sulfur atoms and at least 5 ring members; most preferably the group will contain at least 1 nitrogen atom. The aromatic heterocyclic group can be a single or multiringed group. It will be attached to the sulfur atom in formulas II and V through a carbon atom in the heterocyclic ring.

The particular acylamino group ($R_1$—NH) in the 4-position of the azetidin-2-one of formula II will not affect the photolytic reaction of this invention. Furthermore, 7-acylamino groups have been widely, and generally, disclosed in the cephalosporin art. Preferred acylamino groups ($R_1$-NH-) for use in this invention have the formula

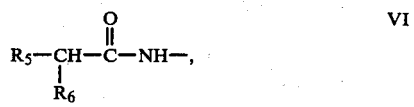

wherein $R_5$ can be phenyl; phenoxy; mono- or disubstituted phenyl or phenoxy (wherein the substituents can be hydroxy, halogen, alkyl of 1 to 4 carbon atoms or alkoxy of 1 to 4 carbon atoms); thienyl, furyl; pyridyl; monosubstituted thienyl, furyl, or pyridyl (wherein the substituent can be alkyl of 1 to 4 carbon atoms or halogen); cycloalkyl having 3 to 7 carbon atoms; cycloalkenyl having 3 to 7 carbon atoms; or cycloalkadienyl having 6 or 7 carbon atoms; and $R_6$ can be hydrogen; hydroxy; amino; carboxy; or ureido.

The following examples are specific embodiments of this invention.

EXAMPLE 1

N-Phenylacetyl-7-amino-3-methylenecepham-4-carboxylic acid trichloroethyl ester.

A solution of 2,2,2-trichloroethyl-4-(benzothiazol-2-yl)dithio-3-(2-phenylacetamido)-α-isopropenylazetidin-2-one-1-acetate (1 mmol) in methylene chloride (300 ml) is placed in a conventional Pyrex photochemical reactor, and photolyzed using a 450 watt medium pressure Hanovia lamp while argon is bubbled through the reactants. After two hours the light source is extinguished and bubbling of argon is continued for ten minutes. The reaction mixture is concentrated to dryness under reduced pressure to yield an orange oil. Silica gel chromatography affords the product as a white crystalline solid. Recrystallization from methylene chloride:ether:hexane provides an analytical sample, m.p. 149°-150° C. dec.; mass spectrum m/e 464 (M+); pmr δ(CHCl₃) 3.42 (d of d, 2H, J=7,14), 362 (S, 2H), 4.68 (d of d, 2H, J=1), 5.17 (S,1H), 5.23 (d,2H,J=4), 5.38 (d,1H,J=4), 5.68 (d of d,1H,J=5,8), 6.15 (d,1H,J=10), 7.40 (S,5H); I.R. (KBr) 3300, 1765, 1760, 1660 cm⁻¹; Analysis calculated for: $C_{18}H_{17}N_2O_4Cl_3S$: C, 46.61; H, 3.69; N, 6.04; S, 6.91; Cl, 22.93. Found: C, 46.84; H, 3.80; N, 5.89; S, 8.02; Cl, 22.89.

EXAMPLE 2

N-Phenoxyacetyl-7-amino-3-methylenecepham-4-carboxylic acid trichloroethyl ester.

A solution of 2,2,2-trichloroethyl-4-(benzothiazol-2-yl)-dithio-3-(3-phenoxyacetamido)-α-isopropenylazetidin-2-one-1-acetate (0.64 mmol) in methylene chloride (750 ml) is placed in a conventional Pyrex photochemical reactor, and photolyzed using a 450 watt medium pressure Hanovia lamp, while argon is bubbled through the reactants. After two hours the light is extinguished and bubbling of argon is continued for ten minutes. The reaction mixture is concentrated to dryness under reduced pressure to yield a brown oil. Silica gel chromatography (φH/EtOAc, 3:1) affords an oil, pmr δ(CDCl₃) 3.58 (d of d,J=7,14), 4.60 (S), 4.85 (S), 5.18 (m), 5.55 (d,J=4), 5.82 (d of d,J=4,8), 7.2 (m); I.R. (CHCl₃), 1780, 1765, 1695 cm⁻¹; mass spectrum m/e 478 (M+).

EXAMPLES 3-15

Following the procedure of Example 1, but substituting the azetidin-2-one derivative shown in column I for 2,2,2-trichloroethyl-4-(benzothiazol-2-yl)dithio-3-(2-phenylacetamido)-α-isopropenylazetidin-2-one-1-acetate, yields the 3-methylene cephalosporin shown in column II.

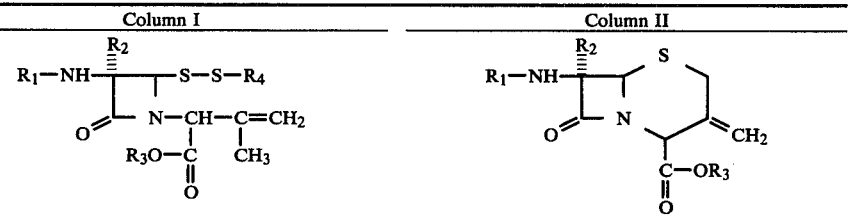

| Example | $R_1$ | $R_2$ | $R_3$ | $R_4$ | $R_1$ | $R_2$ | $R_3$ |
|---|---|---|---|---|---|---|---|
| 3 | phenoxyacetyl | H | H | 2-benzothiazolyl | phenoxyacetyl | H | H |
| 4 | phenylacetyl | H | 2,2,2-trichloroethyl | 5-methyl-1,3,4-thiadiazol-2-yl | phenylacetyl | H | 2,2,2-trichloroethyl |
| 5 | α-amino-α-(1,4-cyclohexadien-1-yl)acetyl | H | H | 2-benzoxazolyl | α-amino-α-(1,4-cyclohexadien-1-yl)acetyl | H | H |
| 6 | phenoxyacetyl | α-CH₃O | 4-methoxybenzyl | 2-benzothiazolyl | phenoxyacetyl | α-CH₃O | 4-methoxybenzyl |
| 7 | phenoxyacetyl | H | 4-nitrobenzyl | 4-pyrazolyl | phenoxyacetyl | H | 4-nitrobenzyl |

-continued

| | Column I | | | | Column II | | |
|---|---|---|---|---|---|---|---|
| Example | R₁ | R₂ | R₃ | R₄ | R₁ | R₂ | R₃ |
| 8 | phenylacetyl | H | 2,2,2-tricholoroethyl | 2-pyrazinyl | phenylacetyl | H | 2,2,2-trichloroethyl |
| 9 | α-amino-α-phenylacetyl | H | H | 2-furyl | α-amino-α-phenylacetyl | H | H |
| 10 | α-phenyl-α-ureidoacetyl | H | trimethylsilyl | 2-pyridyl | α-phenyl-α-ureidoacetyl | H | trimethylsilyl |
| 11 | phenylacetyl | α-CH₃O | 2,2,2-trichloroethyl | 2-thiazolyl | phenylacetyl | α-CH₃O | 2,2,2-trichloroethyl |
| 12 | 2-furylacetyl | H | t-butyl | 2-pyrrolyl | 2-furylacetyl | H | t-butyl |
| 13 | phenylacetyl | H | 2,2,2-trichloroethyl | 2-indolyl | phenylacetyl | H | 2,2,2-trichloroethyl |
| 14 | phenylacetyl | H | benzyl | 2-benzothiazolyl | phenylacetyl | H | benzyl |
| 15 | phenoxyacetyl | α-CH₃O | methyl | 2-quinolinyl | phenoxyacetyl | α-CH₃O | methyl |

What is claimed is:

1. A process for the conversion of an azetidin-2-one derivative having the formula

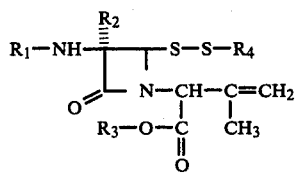

to a 3-methylenecepham having the formula

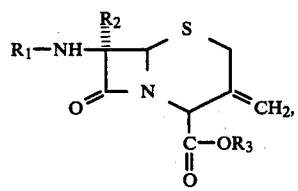

which comprises the photolytic conversion of the azetidin-2-one derivative to the 3-methylenecepham by exposing the azetidin-2-one derivative to a light source emitting light of a wavelength that the azetidin-2-one derivative absorbs; wherein $R_1$ is acyl, $R_2$ is hydrogen or α-methoxy, $R_3$ is hydrogen, alkyl, 2,2,2-trichloroethyl, trimethylsilyl, diphenylmethyl, benzyl, 4-methoxybenzyl, or 4-nitrobenzyl, and $R_4$ is an aromatic heterocyclic group.

2. A process in accordance with claim 1 wherein the light source emits light having a wavelength of 230 nanometers to 500 nanometers.

3. A process in accordance with claim 1 wherein the aromatic heterocyclic group $R_4$ contains at least 5 ring members.

4. A process for the conversion of an azetidin-2-one derivative having the formula

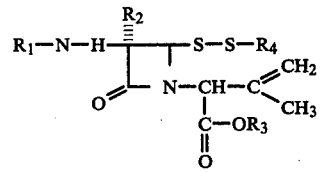

to a 3-methylene cepham having the formula

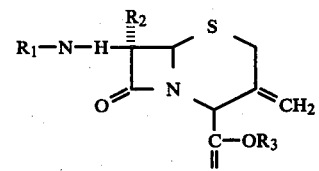

which comprises irradiating with ultraviolet radiation, in an organic solvent, the azetidin-2-one derivative wherein $R_1$ is acyl, $R_2$ is hydrogen or α-methoxy, $R_3$ is hydrogen, alkyl of 1 to 4 carbon atoms, 2,2,2-trichloroethyl, trimethylsilyl, diphenylmethyl, or 4-methoxybenzyl, and $R_4$ is an aromatic heterocyclic group.

* * * * *